(12) United States Patent
Duckett, III et al.

(10) Patent No.: US 11,497,389 B2
(45) Date of Patent: Nov. 15, 2022

(54) ATTACHMENT SYSTEM FOR CONDITIONING LIGHT BETWEEN ENDOSCOPE AND CAMERA

(71) Applicant: KARL STORZ Imaging, Inc., Goleta, CA (US)

(72) Inventors: George E. Duckett, III, Castaic, CA (US); Marios Kyperountas, Goleta, CA (US)

(73) Assignee: KARL STORZ Imaging, Inc., Goleta, CA (US)

(*) Notice: Subject to any disclaimer, the term of this patent is extended or adjusted under 35 U.S.C. 154(b) by 1079 days.

(21) Appl. No.: 16/150,964

(22) Filed: Oct. 3, 2018

(65) Prior Publication Data
US 2020/0107710 A1 Apr. 9, 2020

(51) Int. Cl.
| | | |
|---|---|---|
| *A61B 1/00* | (2006.01) | |
| *A61B 1/055* | (2006.01) | |
| *G02B 27/28* | (2006.01) | |
| *H04N 5/225* | (2006.01) | |
| *A61B 1/04* | (2006.01) | |
| *A61B 1/06* | (2006.01) | |
| *G02B 27/10* | (2006.01) | |

(52) U.S. Cl.
CPC ............ *A61B 1/055* (2013.01); *G02B 27/283* (2013.01); *H04N 5/2258* (2013.01); *A61B 1/00193* (2013.01); *A61B 1/042* (2013.01); *A61B 1/0646* (2013.01); *G02B 27/1066* (2013.01); *H04N 5/2254* (2013.01); *H04N 2005/2255* (2013.01)

(58) Field of Classification Search
CPC ........... A61B 1/055; A61B 1/04; A61B 1/042; A61B 1/045; A61B 1/00004; A61B 1/00006; A61B 1/00105; A61B 1/00009; A61B 1/00059; A61B 1/00066; A61B 1/00163; A61B 1/00121; A61B 1/00131; A61B 1/00137; A61B 1/00195; A61B 1/00197; A61B 1/002; G02B 27/283
USPC ................................ 600/109, 112, 172, 174
See application file for complete search history.

(56) References Cited

U.S. PATENT DOCUMENTS

| | | | |
|---|---|---|---|
| 4,478,212 A | 10/1984 | Asano | |
| 4,781,448 A | 11/1988 | Chatenever | |
| 4,807,594 A | 2/1989 | Chatenever | |
| 4,857,724 A | 8/1989 | Snoeren | |
| 4,858,001 A | 8/1989 | Milbank | |
| 4,862,199 A | 8/1989 | Centkowski | |
| 4,905,082 A * | 2/1990 | Nishigaki | A61B 1/00105 348/73 |
| 5,216,512 A | 6/1993 | Bruijns | |

(Continued)

FOREIGN PATENT DOCUMENTS

| | | |
|---|---|---|
| JP | 2004313523 | 11/2004 |
| WO | 2013010167 A2 | 1/2013 |

*Primary Examiner* — Ryan N Henderson
*Assistant Examiner* — Pamela F Wu
(74) *Attorney, Agent, or Firm* — David Noel Villalpando

(57) ABSTRACT

Medical imaging camera head attachment devices and methods are provided using light captured by an endoscope system or other medical scope or borescope. Various camera head attachments are provided with a camera head design and system allowing recognition of the attachments, and enabling processing algorithms associated with each. The camera head optics are designed to work with a variety of attachments. Several attachments optical designs are provided.

16 Claims, 13 Drawing Sheets

(56) References Cited

U.S. PATENT DOCUMENTS

| | | | |
|---|---|---|---|
| 5,689,365 A | | 11/1997 | Takahashi |
| RE36,434 E | * | 12/1999 | Hamlin ................. A61B 1/042 |
| | | | 600/125 |
| 6,554,765 B1 | | 4/2003 | Yarush |
| 6,659,940 B2 | | 12/2003 | Adler |
| 8,194,122 B2 | | 6/2012 | Amling |
| 8,599,250 B2 | | 12/2013 | Amling et al. |
| 8,784,301 B2 | | 7/2014 | McDowall |
| 8,988,539 B1 | | 3/2015 | Pascoguin |
| 8,994,802 B2 | | 3/2015 | Suga |
| 9,510,739 B2 | | 12/2016 | Adler |
| 9,554,692 B2 | | 1/2017 | Levy |
| 9,706,903 B2 | | 7/2017 | Kimma |
| 2008/0208006 A1 | | 8/2008 | Farr |
| 2012/0281135 A1 | | 11/2012 | Gebhardt |
| 2013/0100264 A1 | * | 4/2013 | Kazakevich ....... G02B 23/2469 |
| | | | 348/68 |
| 2017/0351103 A1 | | 12/2017 | Duckett |

\* cited by examiner

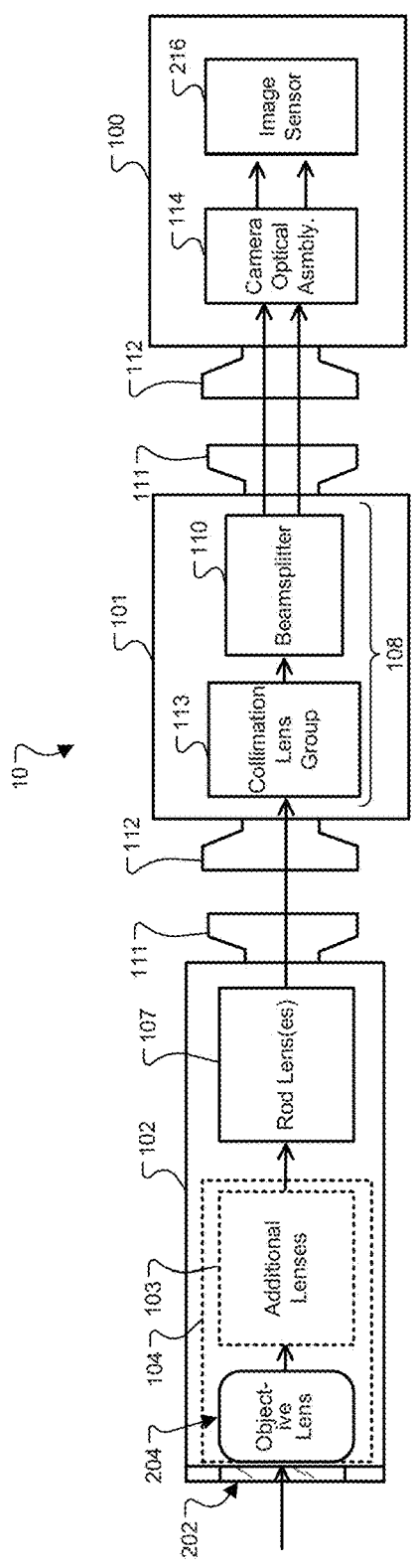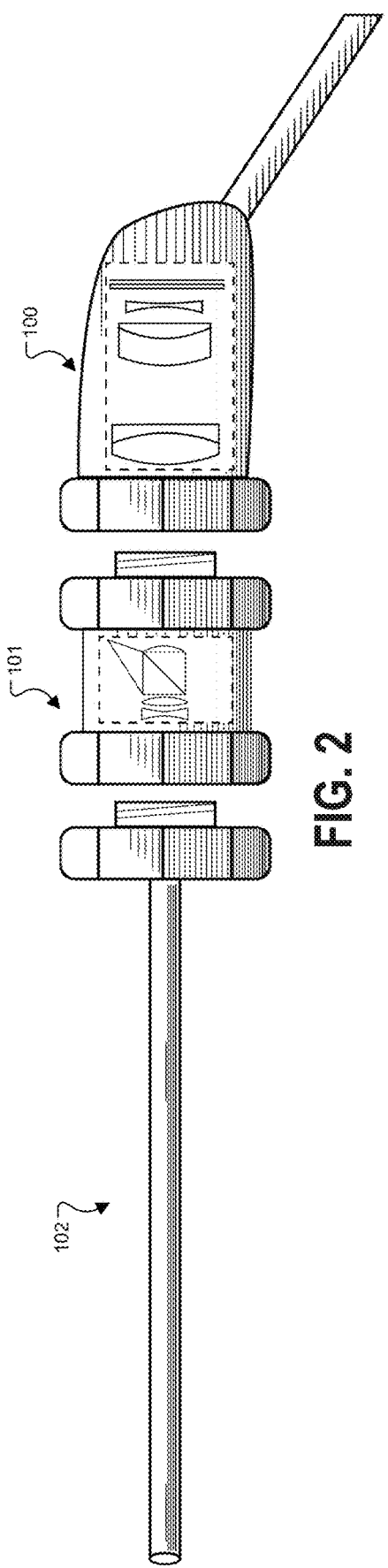

ATTACHMENT SYSTEM FOR CONDITIONING LIGHT BETWEEN ENDOSCOPE AND CAMERA

TECHNICAL FIELD OF THE INVENTION

The invention relates generally to the field of medical image capture and more specifically to endoscopic camera attachments.

BACKGROUND OF THE INVENTION

Dual image acquisition can be a useful feature in the field of endoscopy. Often an endoscope and accompanying camera head must be greatly specialized and customized to provide dual imaging capabilities. Two still images or video streams of the same scene are captured, but each of the captured image streams has different associated characteristics such as a variation in light spectrum, depth of field, or light intensity. In prior dual image systems, images have generally been collected, split in image space, and then focused onto two independent detectors. Such a configuration allows for versatility than a single image acquisition system, but is generally more expensive and complex than single image systems, requiring at least two sensors and associated electronics and mounting assemblies.

Further, the cost of a dual image system may be higher due to the duplication of certain optical components used in focusing and detecting the image light of the dual channels.

What is needed are devices and methods to enable an endoscopic camera to acquire dual images in a cost-effective manner. What is further needed are devices allowing the use of varied existing endoscopes for dual imaging applications, and allowing the detection of the varied characteristics in the dual images.

SUMMARY OF THE INVENTION

It is an object of the invention to provide improved endoscope acquisition of dual images, and to allow the use of varied camera head attachments for dual imaging applications and conventional endoscopic imaging. It is another object to make the most effective use of high definition image sensors in dual imaging applications. It is a further object of the invention to allow detection of varied characteristics in the dual images, based on ability to vary the characteristics of the optical channels of the dual images.

To accomplish these and other objects, endoscopic camera head devices and methods are provided using light captured by an endoscope system through various camera head attachments. The camera head provides recognition of the attachments, and the enabling of processing algorithms associated with each. The camera head optics are designed to work with a variety of attachments. The designs for several optical attachments are provided.

According to a first aspect of the invention, a system is provided for modifying light passing from a medical scope to a camera. The system includes a camera and a first light conditioning attachment, and may include a camera control unit. The light conditioning attachment includes a body with an optical portal, the body adapted to be attached to and detached from the camera and the medical scope, with an optical portal positioned to allow light from the medical scope to pass from the medical scope to a camera light sensor. An optical assembly is optically positioned in the light conditioning attachment, including a collimation lens group and an optical group including a beam splitter or a pupil splitter. The collimation lens group is operable to receive image light from the medical scope in a substantially afocal state and increase collimation of the image light through refraction. The optical group is operable to receive the image light from the collimation lens group and with the image light substantially afocal, split the image light into a first portion of image light and a second portion of image light, and direct the first portion of image light along a first optical path and the second portion of image light along a second optical path. The attachment includes an identification indicator adapted to be recognized by the camera or a camera control unit. The camera further includes a lens aperture sized to receive light from the first and second optical paths, and a lens group operable to focus the first portion of image light on a first area of an image sensor and focus the second portion of image light on a second portion of the image sensor separate from the first portion. The camera control unit is adapted to recognize, by means of the identification indicator, when the first light conditioning attachment is attached to the camera and when a second light conditioning attachment is attached to the camera, and in response to recognizing the first light conditioning attachment, selecting and enabling image processing algorithms specific to the first light conditioning attachment for processing image data from the image sensor.

According to some implementations of the first aspect, the system includes the second light conditioning attachment, wherein the second light conditioning attachment has a different light conditioning function, and a different associated identification indicator, than the first light conditioning attachment.

According to some implementations of the first aspect, the beamsplitter of the first light conditioning attachment is operable to split the image light with spectral selectivity, whereby the spectral content of the first portion of image light differs substantially from the spectral content of the second portion of image light. The first portion of image light may include infrared content with the second portion of image light including visible light.

According to some implementations of the first aspect, the first light conditioning attachment includes a pupil splitter adapted to split the image light with the pupil splitter into the first portion of image light and the second portion of image light, thereby enabling the camera to provide 3D imaging.

According to some implementations of the first aspect, the first light conditioning attachment's optical assembly further includes, along the first optical path, a lens selected to alter a focal plane of an image produced by the first portion of image light relative to a focal plane of an image produced by the second portion of image light, thereby enabling the camera to provide extended depth of field imaging. In some implementations, the camera's lens group includes a Petzval lens and a field flattener.

According to some implementations of the first aspect, the attachment includes a magnifying element in the first optical path such that the first and second portions of image light have different magnifications.

According to some implementations of the first aspect, the first light conditioning attachment is configured such that the first and second portions of image light have different intensities, enabling thereby high dynamic range imaging.

According to a second aspect of the invention, a method is provided for producing endoscopy images. The method includes, on an electronic processor associated with a camera head, recognizing that a first light conditioning attachment has been attached to the camera head. In response, the method selects and enables image processing algorithms in a camera control module, the image processing algorithms specific to the first light conditioning attachment and configured for processing image data from an image sensor on the camera head. The method includes directing image light from a medical scope along a single optical channel to the first light conditioning attachment, receiving the image light in the attachment in a substantially afocal state, and increasing collimation of the image light through refraction. In the first light conditioning attachment, the method splits the image light from the single optical channel into a first portion of image light and a second portion of image light, and directs the first portion of light along a first optical path and the second portion of image light along a second optical path. In the camera head, the method receives the image light through a lens aperture sized to receive light from the first and second optical paths, and focuses the first portion of image light on a first area of an image sensor while focusing the second portion of image light on a second portion of the image sensor separate from the first portion. The method transmits image data from the image sensor to a camera control module and, on the camera control module, processes the image data from the image sensor according to the enabled image processing algorithms.

According to some implementations of the second aspect, recognizing that a first light conditioning attachment has been attached to the camera head may include reading an RFID identifier from the first light conditioning attachment, reading an optical identifier tag for the first light conditioning attachment, or receiving an electronic identification signal from the first light conditioning attachment.

According to some implementations of the second aspect, the method further includes, on the electronic processor, recognizing that a second light conditioning attachment has been attached to the camera head, and in response selecting and enabling second image processing algorithms in the camera control module. The second image processing algorithms specific to the second light conditioning attachment and configured for processing image data from the image sensor.

According to some implementations of the second aspect, the method further includes spectral filtering the image light whereby the spectral content of the first portion of light differs substantially from the spectral content of the second portion of light. The first portion of light may include infrared content with the second portion of light including visible light.

According to a third aspect of the invention, an endoscopic imaging system includes an endoscopic camera head, an endoscopic camera control unit, and two or more light conditioning attachments. Each of the attachments includes a body, with an identification indicator in the body adapted to be recognized by the camera head or camera control unit. The attachment has a proximal end adapted to be attached to and detached from a camera distal end, a distal end adapted to be attached to and detached from a medical scope. The attachment also includes an optical portal positioned to allow light to pass from the medical scope toward a camera image sensor, and an optical assembly optically positioned between the proximal and distal ends of the attachment. The optical assembly includes a collimation lens group, and an optical group. The system includes at least two attachments selected from a group of various attachment designs with different optical groups providing different functions. The various designs are:

a beam splitter optical group operable to receive image light from the collimation lens group, and with the image light substantially afocal, split the image light into a first portion of light and a second portion of light, and direct the first portion of light along a first optical path and the second portion of light along a second optical path;

a conventional imaging optical group operable to receive image light from the collimation lens group, and with the image light substantially afocal to resize the image light;

a 3D imaging optical group operable to receive image light from the collimation lens group, and with the image light substantially afocal, to split it with a pupil splitter into the first portion of image light and the second portion of image light, thereby enabling the camera to provide images for 3D imaging;

a high dynamic range optical group operable to receive image light from the collimation lens group and, with the image light substantially afocal, split the image light unequally by intensity with a beam splitter, such that the first and second portions of image light have different intensities;

a depth of field enhancing optical group operable to receive image light from the collimation lens group, and with the image light substantially afocal, split the image light with a beam splitter into a first portion of image light and a second portion of image light, and direct the first portion of image light along a first optical path and the second portion of image light along a second optical path, one of the optical paths including a lens selected to alter a focal plane of an image produced by the first portion of light relative to a focal plane of an image produced by the second portion of light, thereby enabling the camera head to provide images for extended depth of field imaging;

a magnification enhancing optical group operable to receive image light from the collimation lens group, and with the image light substantially afocal, split the image light with a beam splitter into a first portion of image light and a second portion of image light, and direct the first portion of light along a first optical path and the second portion of light along a second optical path, one of the optical paths including a magnification lens, such that one portion of light has a higher magnification than the other; and a spectrally selective optical group operable to receive image light from the collimation lens group, and with the image light substantially afocal, split the image light with a spectrally selective beam splitter into a first portion of image light and a second portion of image light, whereby the spectral content of the first portion of image light differs substantially from the spectral content of the second portion of image light.

According to some implementations of the third aspect, the endoscopic camera control unit is further operable to, in response to receiving an indication that a first light conditioning attachment has been attached to the camera head, select and enable image processing algorithms specific to the first light conditioning attachment and configured for processing image data from the camera image sensor.

These and other features of the invention will be apparent from the following description of the preferred embodiments, considered along with the accompanying drawings.

BRIEF DESCRIPTION OF THE DRAWINGS

The present invention will become more fully understood from the detailed description given herein and the accompanying drawings which are given by way of illustration only, and thus are not limitative of the present invention, and wherein:

FIG. 1 is a block diagram of a medical imaging system according to an example embodiment of the invention including a beamsplitter attachment;

FIG. 2 is a partial cutaway side view of a system similar to that of FIG. 1, but includes threaded connections between the elements;

DETAILED DESCRIPTION OF EXAMPLE EMBODIMENTS

Figure 3:
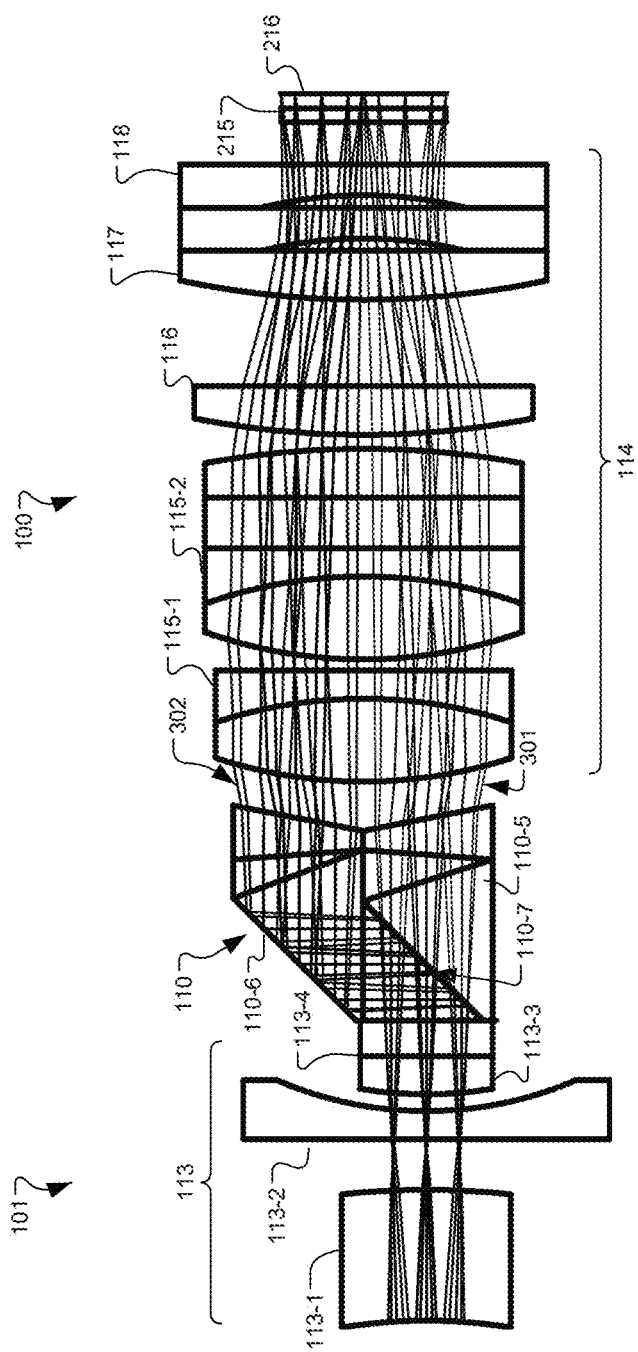
FIG. 3 is a cross section diagram of an optical assembly of a camera head and attachment according to another embodiment including a beamsplitter attachment.

As used herein, first elements (e.g., sensors and lenses) that are "optically arranged" in relation to other elements, refers to the first elements' position along a common optical path that includes first and other elements. For example, a lens group optically arranged between an image sensor and an objective, means that the lens group occupies a portion of the optical path that light travels (e.g., from the objective to the image sensor) for capturing images or video. Directions such as upstream and downstream refer to the direction of light travel.

Because digital cameras, image sensors and related circuitry for signal capture and processing are well-known, the present description will be directed in particular to elements forming part of, or cooperating more directly with, a method and apparatus in accordance with the invention. Elements not specifically shown or described herein are selected from those known in the art. Certain aspects of the embodiments to be described are provided in software. Given the system as shown and described according to the invention in the following materials, software not specifically shown, described or suggested herein that is useful for implementation of the invention is conventional and within the ordinary skill in such arts.

FIG. 1 is a block diagram of a medical imaging system 10 according to an example embodiment of the invention. Medical imaging system 10 ("system 10") includes a camera head 100, a light conditioning attachment 101 ("attachment 101") and an endoscope 102. The proximal side of attachment 101 is attached to camera head 100 via distal and proximal connectors 111 and 112, and endoscope 102 is similarly attached to the distal side of attachment 101. Connectors 111 and 112 in this embodiment are standard eyecup style optical connectors but may be any suitable connector allowing light to pass from endoscope 102 to camera head 100. For example, the system of FIG. 2 uses threaded connections on both sides of attachment 101. Various structural components supporting the depicted elements are omitted in the diagrams herein, as well as other components such as illumination sources and controls, which are known in the art and are not shown in order to avoid obscuring the relevant details of the example embodiments of the invention.

Attachment 101 includes a collimating lens or lens group 113 positioned at or behind a central window of its distal connector 112 to receive and condition optical image light from the endoscope 102. By the term "substantially afocal," it is meant that the attachment optical group 108 as a whole does not have a significant focusing effect on the imaging light passing there through, and, in addition, the attachment optical group 108 is not positioned in the image space of the optical system, and so does not receive focused image light. A beamsplitter 110 is optically arranged to receive the optical image light in a substantially afocal state from the endoscope 102, passing through collimating lens group 113, and split the optical image light into a first portion of light directed to a first optical path and a second portion of light directed to a second optical path as depicted by the two arrows showing the light path to common camera head optical group 114 ("optical group," "optical assembly"). The first and second optical paths are further described with respect to the example embodiments below. The use of attachments 101 for splitting the afocal light ahead of the camera head optical group 114, rather than in the image space after the light is focused, has the advantage of allowing a common back end to be used with various alternate designs for optical group 108 having disparate functions, simplifying the optical design, development, and construction of the camera head. The use of a common image sensor allows efficient use of high resolution sensors, which provide enough pixel resolution to capture a plurality of images with sufficient resolution for many endoscope applications. Enhanced depth-of-field, high dynamic range (HDR), fluorescence imaging (FI) analysis (including indocyanine green (ICG) analysis), and polarization studies can benefit from the collection of varying versions of the same image. A further advantage is that the attachment may be used with a basic endoscope head allowing the pairing of stock endoscopes with a plurality of possible inventive imaging devices utilizing different attachment optical assemblies 108 for a variety of different applications.

The camera head optical group 114 is generally for focusing the substantially afocal light received from optical assembly 108 onto the image sensor. Camera head optical group 114 includes refractive elements optically arranged to receive the first and second portions of light from the beamsplitter 110 and focus the first portion as a first image onto a first area of a common image sensor 216 and the focus second portion as a second image onto a second area the common image sensor 216, different from the first area. The camera head optical group 114 typically includes at least one focusing lens, with the group having a total positive power. Many suitable lenses and combinations of lenses may be used for camera head optical group 114.

In some embodiments, system 10 includes an endoscope 102 as depicted at the left of the block diagram. The depicted endoscope is an example only, and many endoscope and borescope designs are suitable, including rigid and flexible endoscopes and borescopes. Endoscope 102 includes a cover glass 202 at its distal tip, which in this version faces directly along the longitudinal axis of the endoscope 102, but may also be positioned at an angle relative to the longitudinal axis as is known in the art. Behind, or on the proximal side of, the cover glass 202 is shown a preferred position for the objective lens 204, set against or very near cover glass 202 and preferably assembled together with the cover glass in construction. While a wide-angle lens is preferred for objective lens 204, this is not limiting, and any suitable lens may be used in various embodiments. Objective lens 204 may be part of an objective lens group 104 which may include one or more additional lenses 103. The particular number and arrangement of lenses in the endoscope 102 will vary widely depending on the application. Optically arranged or attached at the proximal side of objective lens 204 or objective lens group 104 is a series of one or more rod lenses 107 that serve to pass the light down endoscope 102 towards its proximal end. Typically, several rod lenses 107 are employed, which may be separated by spacers or other lenses in any suitable manner known in the art. Also, while the endoscope 102 is typically rigid, known shaft design variations allow rod lenses to be used in a semi-flexible shaft in which flexible joints are present at one or more places along the shaft between the rod lenses while the shaft is rigid along the portions containing a rod lens. Such a shaft design may be used in various embodiments of the invention. FIG. 2 is a partial cutaway side view of a system similar to that of FIG. 1, but including threaded connections between elements 100, 101, and 102.

Figure 4:
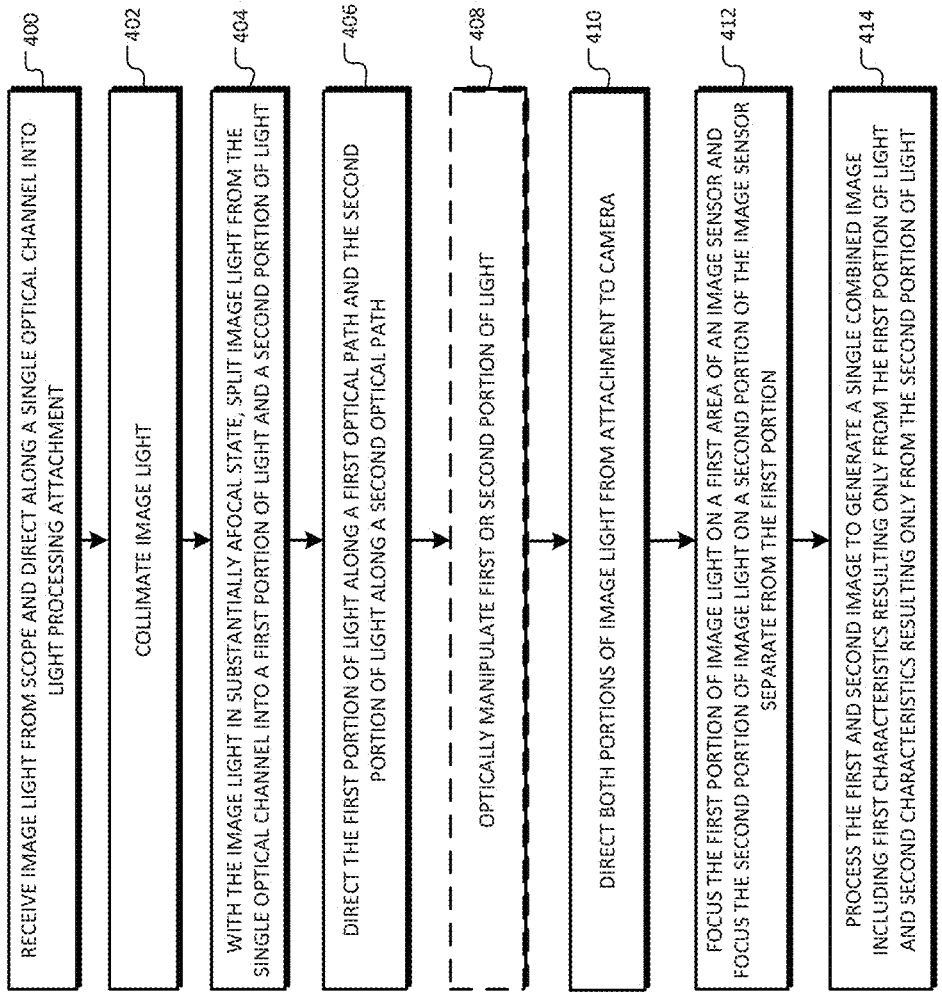
FIG. 4 is a flowchart of a process of using the arrangement of FIGS. 1-3 with an endoscope after configuration.

FIG. 3 is a cross section diagram of an optical assembly of a camera head and attachment according to another embodiment, also including a light ray diagram showing the passage of image light through the optical assemblies to image sensor 216. The depicted optical elements are in diagram form only and are not drawn to scale. FIG. 4 is a flowchart of a process of using the arrangement of FIG. 3 with an endoscope. Referring to both figures, attachment 101's optical assembly 108 starts at collimating lens group 113 which receives light entering attachment 101 from an attached endoscope. The image light is received from the scope and directed in a single optical channel of attachment 101 (block 400, FIG. 4) to collimating lens group 113. Collimating lens group 113 may have a slightly positive or negative power in order to adjust the image light to the desired condition to be received by beamsplitter 110 (block 402). Collimating lens group 113 includes a concave-convex lens 113-1 optically arranged to receive the image light and having a negative optical power spreading the image light to a desired size. Optically arranged in the proximal direction from lens 113-1 is plano-concave lens 113-2, which has a negative optical power to align the image light. Optically arranged along the concave area of lens 113-2 are convex-plano lenses 113-3, with a positive power for further conditioning the light for passage to beamsplitter 110. Lenses 113-1, 113-2, and 113-3 may be referred to as a collimating lens group. A flat plate 113-4 is positioned is optically positioned between lens 113-3 and beamsplitter 110.

Beamsplitter 110 is optically arranged to receive the optical image light in an afocal state from the endoscope 102, via the collimating lens group 113, and split it into a first portion of light directed to a first optical path 301 passing through prism group 110-5, and a second portion of light directed to a second optical path 302 passing through prism group 110-6 (block 404 and 406).

Beamsplitter 110 is constructed of prisms, including a right-angle prism and triangular prism with a joint having suitable partially reflective coating along their adjacent surface at interface 110-7, by which the image light is split with a first portion passing straight through along first optical path 301 and a second portion reflected upward along second optical path 302 as depicted. As discussed above, the first and second portions of light may comprise different spectral content, for example, as a result of the interface 110-7 comprising a dichroic filter, or, alternately by placing a color absorbing filter along optical paths 301 and/or 302. For example, infrared light may be passed through along path 301 while visible imaging light is reflected at interface 110-7 along optical path 302. In other versions, such as a high dynamic range (HDR) attachment 101, interface 110-7 may pass light of lower intensity along one of paths 301 and 302, while passing light of a higher intensity, including the same image, along the other path. Such optical manipulation is shown in the process at block 406. These two paths are then detected at image sensor 216 and employed to produce an HDR image. Beamsplitter 110 is constructed in this embodiment with multiple angled prisms in order to produce a symmetrical arrangement of optical paths 301 and 302 as they are directed toward camera head 100, with each path including a triangular prism and a wedge-shaped prism. This particular arrangement allows the image light to be received by beamsplitter 110 parallel to a longitudinal of both assemblies. Other versions may employ other suitable prism arrangements allowing an optical axis of the attachment 101 optics to be non-parallel to the camera head 100 optical assembly.

A flat portal may also be included between attachment 101 and camera head 100, or the final prisms of beamsplitter 110 may serve as a portal of the attachment passing the light of both optical paths 301 and 302 to camera head 100 (block 410). The optical assembly 114 in camera head 100 in this version includes refractive elements optically arranged in both the first and second optical paths 301 and 302 to receive the first and second portions of light from the beamsplitter 110 and focus the first portion as a first image onto a first area of a common image sensor 216 and the focus second portion as a second image onto a second area the common image sensor 216, different from the first area (block 412). Both optical paths 301 and 302 are incident on a doublet achromat lens 115-1, which has a positive optical power, including a biconvex lens and a concave-plano lens. The camera head 100 optical group is positioned with the axis pointing between the first and second paths such that each path has similar incidence on lens 115-1, symmetrical about the camera head 100 optical group. Optically arranged in the proximal direction to doublet achromat lens 115-1 is a second lens group 115-2 including a doublet lens, a flat plate, and a plano-convex lens, and having a total positive optical power as indicated by the converging effect on the depicted ray lines. While lens assemblies 115-1 and 115-2 are shown, other suitable optical assemblies may be used. For example, the optical assembly may use a Petzval lens or lens group with a field flattener, or other suitable lens or lens group presented at the camera head 100 aperture that is capable of a very large aperture and has a field flattening effect with positive powered elements in front and a negative powered field flattener near the image plane. This is convenient in this system because the two optical paths will be separated at the front lens and the aperture must be large enough to accommodate both. Optically arranged next is a convex-plano lens 116 which further focuses both portions of light toward the sensor.

Optically arranged to receive both portions of light from lens 116 is a lens 117, having a negative power. Optically arranged next are two smaller plano-concave lenses 118 with a negative power, directing both portions of light toward cover glass 215 and image sensor 216. Lenses 118 direct both portions of light to create a pair of images of the desired size at image sensor 216. Finally, the process includes processing the first and second image to generate a single combined image including first characteristics resulting only from the first portion of light and second characteristics resulting only from the second portion of light (block 414). This may be implemented, for example, with image processing hardware as described with respect to FIG. 15.

Figure 5:
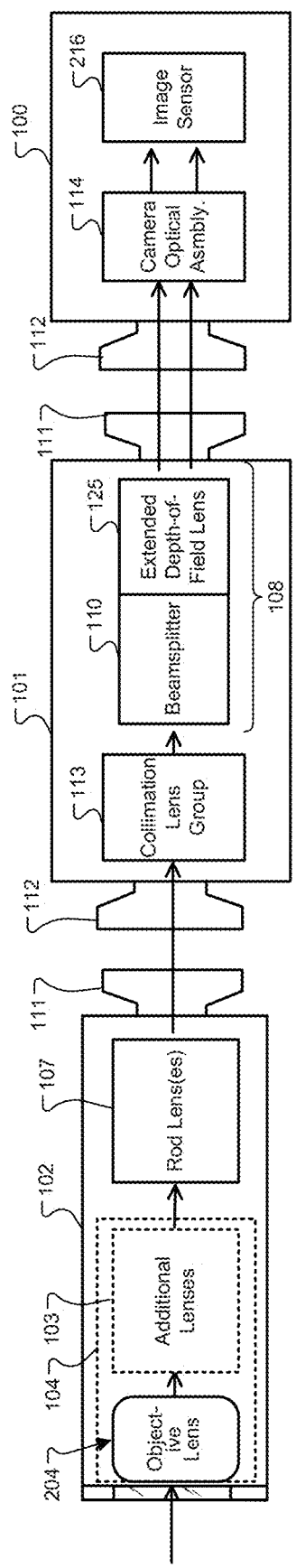
FIG. 5 is a block diagram of a medical imaging system according to another example embodiment of the invention providing an attachment for improving depth-of-field.
Figure 6:
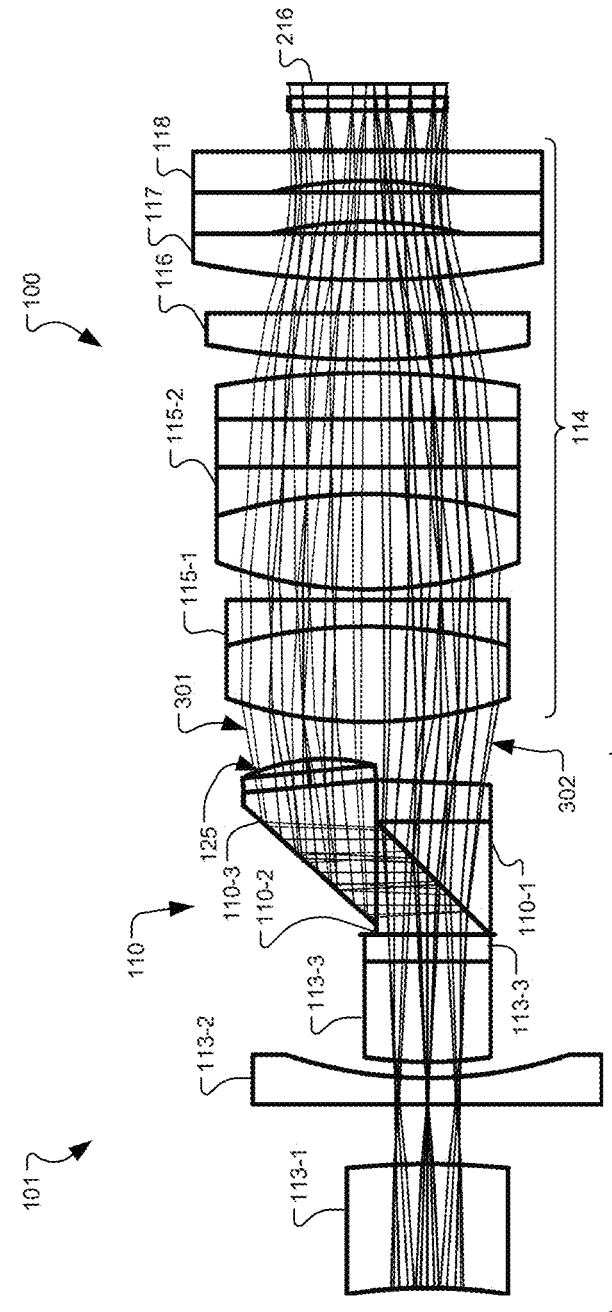
FIG. 6 is a partial cross section diagram of optical assemblies according to the embodiment of FIG. 5.
Figure 7:
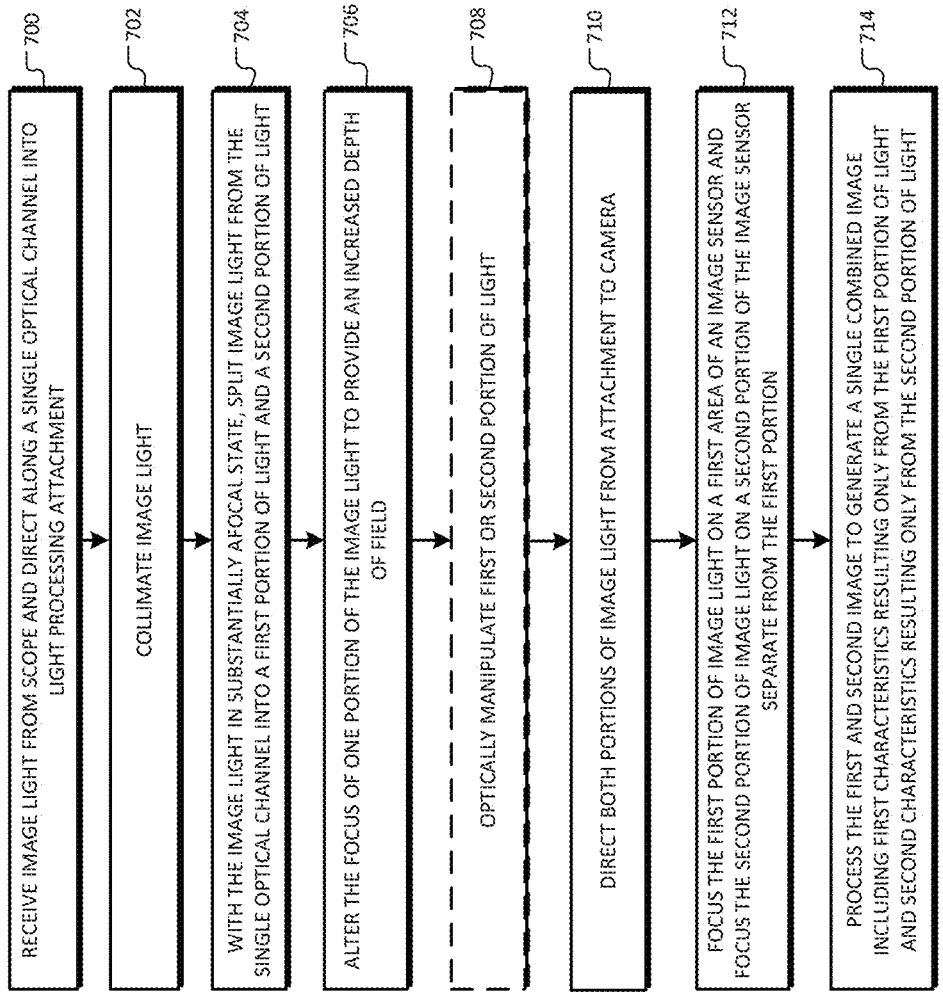
FIG. 7 is a flowchart of a process of operating the embodiment of FIG. 5 following its configuration.

FIG. 5 is a block diagram of a medical imaging system 10 according to another example embodiment of the invention providing an attachment for improving depth-of-field. FIG. 6 is a partial cross section diagram of optical assemblies 114 and 108 from attachment 101 and camera head 100 according to the embodiment of FIG. 5. FIG. 7 is a flowchart of a process of operating this embodiment following its configuration. The depicted systems of FIG. 5 and FIG. 6 are similar to those of FIGS. 1-3, but include an additional extended depth-of-field lens 125 in first optical path 301 to alter path 301's focal depth, as will be further described below. FIG. 6 includes a light ray diagram showing the passage of image light through the optical assemblies 108 and 114 to image sensor 216. As shown in the flowchart, image light is received from endoscope 102 at block 700, and directed along a single optical channel into attachment 101. With the image light in a substantially afocal state, image light from endoscope 102 is received by collimation lenses 113-1, 113-2, and 113-3, and plate 113-4, similar to those described with respect to FIG. 3. As shown at block 702, the light is collimated to a desired state and directed to beamsplitter 110. Beamsplitter 110 is optically arranged to receive the optical image light in an afocal state and split the optical image light into a first portion of light directed to a first optical path 301 and a second portion of light directed to a second optical path 302 (block 704). In this embodiment, beamsplitter 110 is constructed of prisms, including the two lower right-angle prisms 110-2 and 110-3 with a suitable partially reflective coating along their adjacent surface, by which the image light is split with a first portion passing straight through along first optical path 301 and a second portion reflected upward along second optical path 302 as depicted. At block 706, the process alters the focus of one portion of the image light to provide an increased depth-of-field. Such alteration is done by an extended depth-of-field lens 125, in this version a plano-convex lens with a positive optical power, optically arranged in the first optical path 301 to receive the first portion of light from beamsplitter 110 and focus it, providing a modified focus to the image produced from the second portion of light in second path 302. As used herein, an extended depth-of-field lens is not limited to the depicted plano-convex lens, but includes a lens providing a positive or negative focal alteration to one of at least two portions of light where the other(s) either have no alteration or a different alteration, resulting in an extended depth-of-field derived from images formed at one or more image sensors, each image have a different focal depth and therefore include focal characteristics not present in the other image. One or both portions of light may be further optically manipulated at block 708. The two images are combined in processing to create an image with a larger depth-of-field (block 714). The two images may also be employed and displayed separately. Various other optical elements or manipulating optical means may be placed in one of the optical paths such as at the location of lens 125 or optically arranged after prism 110-1 in the second optical path 302. For example, polarization filters, intensity filters, spectral filters, field stops, magnifying lenses, and other optical elements may be used.

Both optical paths 301 and 302 are incident on a doublet achromat lens 115-1, which has a positive optical power, including a biconvex lens and a concave-plano lens. Optical group 114 is positioned with the axis pointing between the first and second paths such that each path has similar incidence on lens 115-1, symmetrical about the camera head 100 optical group. Optically arranged in the proximal direction to doublet achromat lens 115-1 is a second lens group 115-2 including a doublet lens, a flat plate, and a plano-convex lens, and having a total positive optical power as indicated by the converging effect on the depicted ray lines. Optically arranged next is a convex-plano lens 116 which further focuses both portions of light toward the sensor. Optically arranged to receive both portions of light from lens 116 is a convex-plano lens 117, having positive optical power. Optically arranged next are two smaller plano-concave lenses 118 with a negative power, directing both portions of light toward cover glass 215 and image sensor 216. Lenses 118 spread both portions of light create a pair of images of the desired size at image sensor 216.

Figure 8:
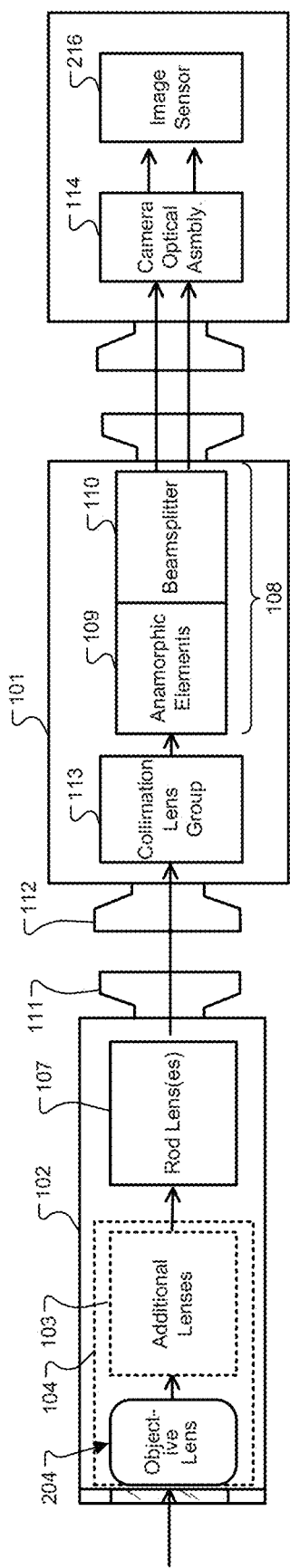
FIG. 8 is a block diagram of a medical imaging system 10 according to another example embodiment of the invention including an attachment for providing anamorphic alteration and beamsplitting.
Figure 9:
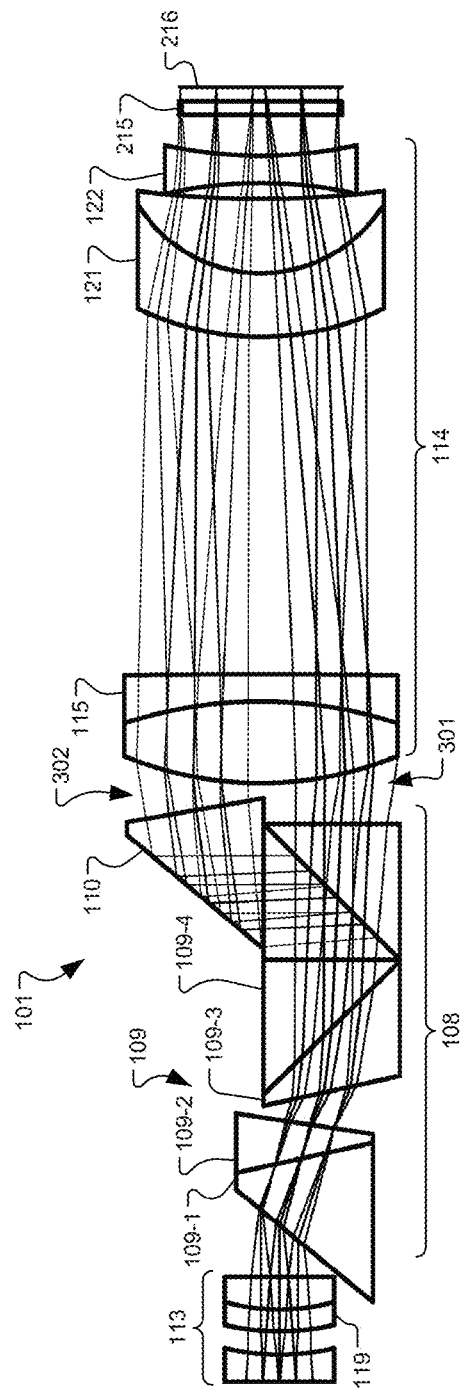
FIG. 9 is a partial cross section diagram according to the embodiment of FIG. 8.
Figure 10:
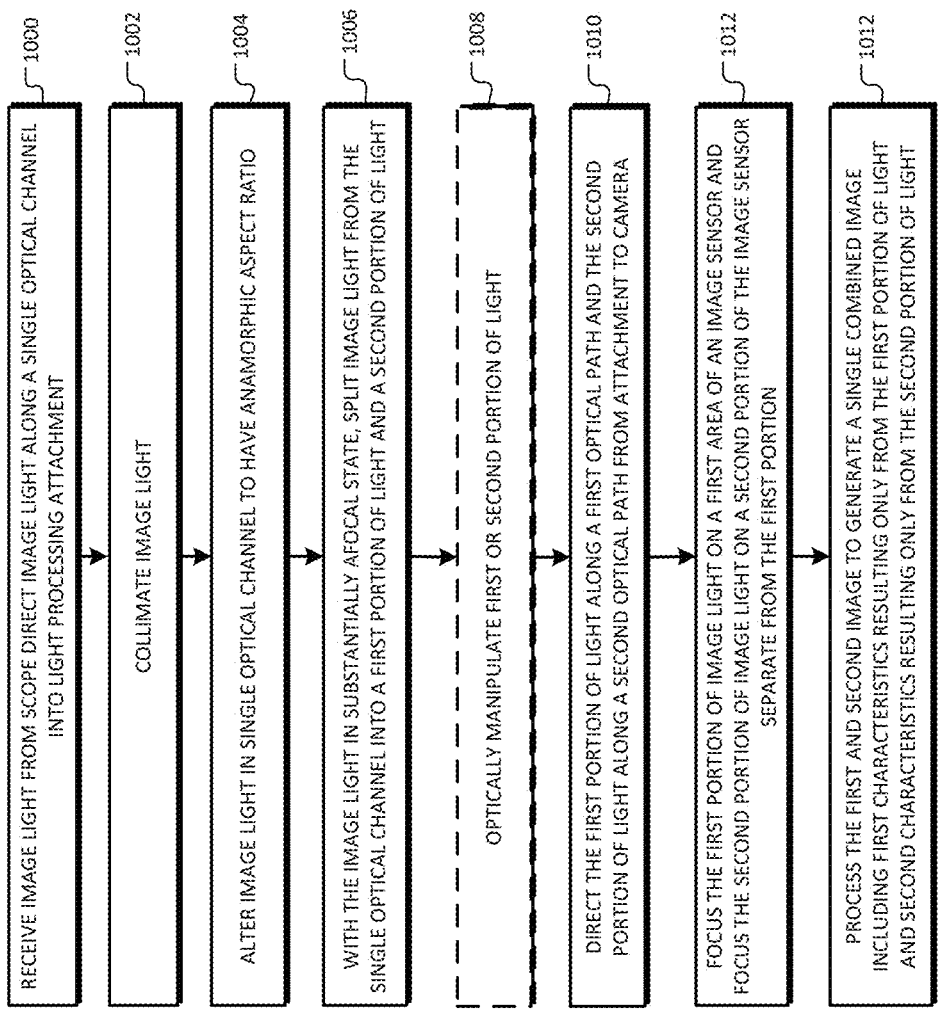
FIG. 10 is a flowchart of a process of operating the embodiment of FIG. 8 following its configuration.

FIG. 8 is a block diagram of a medical imaging system 10 according to another example embodiment of the invention including an attachment for providing anamorphic alteration and beamsplitting. FIG. 9 is a partial cross section diagram of optical assemblies 114 and 108 from attachment 101 and camera head 100 according to the embodiment of FIG. 8. The construction of endoscope 102 is similar to the other embodiments. FIG. 10 is a flowchart of a process of operating this embodiment following its configuration. Referring to FIGS. 8-10, optical assembly 108 starts with a collimating and directing lens group 113, 119 of a single channel where the image light enters attachment 101 (block 1000). In this version the collimating and directing lens group includes a doublet lens 119 optically arranged to receive the image light from lens 113 and produce a collimation effect (block 1002). Doublet lens 119 includes a convex-concave lens and a convex-plano lens. In this version, overall collimating and directing lens group 113, 119 has a positive power for directing the image light in a substantially afocal state toward anamorphic optical elements 109 of optical assembly 108. Optically arranged to receive the image light from lens 119 are anamorphic optical elements 109, which alter the image light to have an anamorphic aspect ratio (block 1004). In contrast to the embodiment shown in FIG. 2, anamorphic optical elements 109 of this embodiment comprise four triangular prisms labeled 109-1 through 109-4. Prisms 109-1 and 109-2 together act as one prism of an anamorphic prism pair, paired with prism 109-3 and 109-4 acting as the other half of the anamorphic prism pair, to enlarge the vertical dimension of the image light while leaving the horizontal dimension (the direction into the page) unchanged. Each element of the pair is a doublet to make it achromatic. Other suitable combinations of prisms, including prism pairs, may be used to provide the desired anamorphic effect.

Beamsplitter 110 is optically arranged to receive the optical image light in an afocal state and split the optical image light into a first portion of light directed to a first optical path 301 and a second portion of light directed to a second optical path 302 (block 1006). In this embodiment, beamsplitter 110 is constructed of prisms, including the two lower right-angle prisms with a suitable partially reflective coating along their adjacent surface, by which the image light is split with a first portion passing straight through along first optical path 301 and a second portion reflected upward along second optical path 302 as depicted. As discussed above, the first and second portions of light may comprise different spectral content. The second portion of light reflects off the reflective inner surface of the upper prism, which in this version is a less-than right-angle prism, to direct the second optical path toward the camera head optical group 114 with optical path 302 slightly diverging from optical path 301 as can be seen in the ray diagram. Further optical elements may be added to one or both of the optical paths, providing a further manipulation of light as shown at block 1008. Next at block 1010, both portions of light are directed out of attachment 101 and into the camera head optical group 114.

The camera head optical group 114 includes refractive elements optically arranged in both the first and second optical paths 301 and 302 to receive the first and second portions of light from the beamsplitter 110 and focus the first portion as a first image onto a first area of a common image sensor 216 and the focus second portion as a second image onto a second area the common image sensor 216, different from the first area. In this embodiment, camera head optical group 114 includes a doublet achromat lens 115 having a positive optical power, including a biconvex lens and a concave-plano lens. As can be understood from the ray diagram, lens 115 and the rest of camera head optical group 114 are symmetrically arranged with respect to the first and second optical paths 301 and 302, and large enough to span both paths. That is, camera head optical group 114 is positioned with the axis pointing between the first and second paths such that each path has similar incidence on lens 115, symmetrical about the central axis of optical group 114. Similarly to the previous embodiment, this is done by positioning the optical axis of optical group 114 to bifurcate the angle between first and second optical paths 301 and 302, although in this embodiment group 114 is not tilted with respect to optical assembly 108. However, in this case the optical paths are diverging. As can be seen on the ray diagram, the positive optical power of doublet lens 115 refracts both optical paths to converge toward doublet lens 121. The doublet lens 121 includes two adjacent convex-concave lenses which further focus both portions of light in the direction of sensor 216. Optically arranged to receive both portions of light from lens 121 is a biconcave lens 122, which has a negative power and serves to reduce the angle of incidence at which the focused image light hits sensor 216 behind cover glass 215. The resulting image data provides two anamorphic images formed on the same image sensor 216, such as those shown in the diagram of FIG. 17B. Generally, the two portions of light at paths 301 and 302 are focused onto separate portions of image sensor 216 (block 1012). The images may include different characteristics either produced by the beamsplitter (such as spectrum, polarization, or intensity) or by additional lenses or filters in one of the first or second paths. For example, an indocyanine green (ICG) imaging filter may be used, which only allows the wavelengths fluoresced by ICG dye (typically the near infrared region) to be passed in a selected one of the first or second optical paths. Such a filter may be included as part of the beamsplitter, with light split along the second optical path by reflective and dichroic surfaces or band-pass/band-reflect properties at the surfaces described. An extended depth-of-field lens may also be employed in this version, optically positioned at the output of beamsplitter 110 in one of the optical paths 301, 302. As with the other embodiments herein, the two images detected at sensor 216 are typically processed by the system camera control unit (CCU) to produce a final image based on both images, including first characteristics resulting only from the first portion of light and second characteristics resulting only from the second portion of light (block 1014). However, for some applications the individual captured images may be displayed as may a combination of a single resultant image along with the generally unprocessed individual images.

Figure 11:
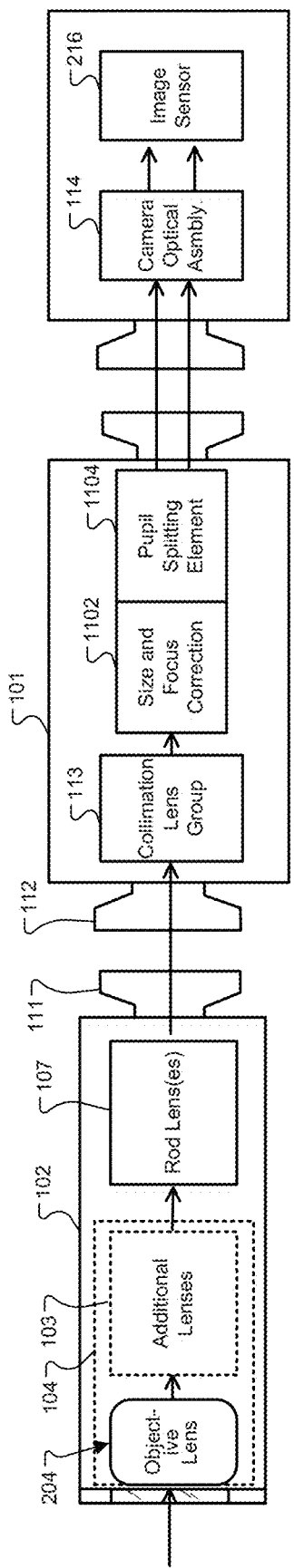
FIG. 11 is a block diagram of a medical imaging system according to another example embodiment of the invention providing an attachment with a pupil-splitting function allowing 3D imaging to be performed.
Figure 12:
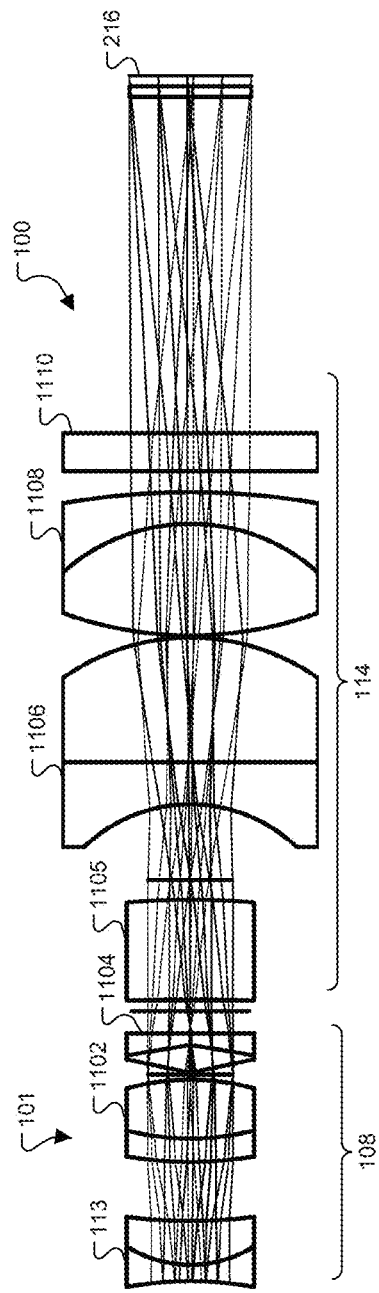
FIG. 12 is a partial cross section diagram of optical assemblies according to the embodiment of FIG. 11.
Figure 13:
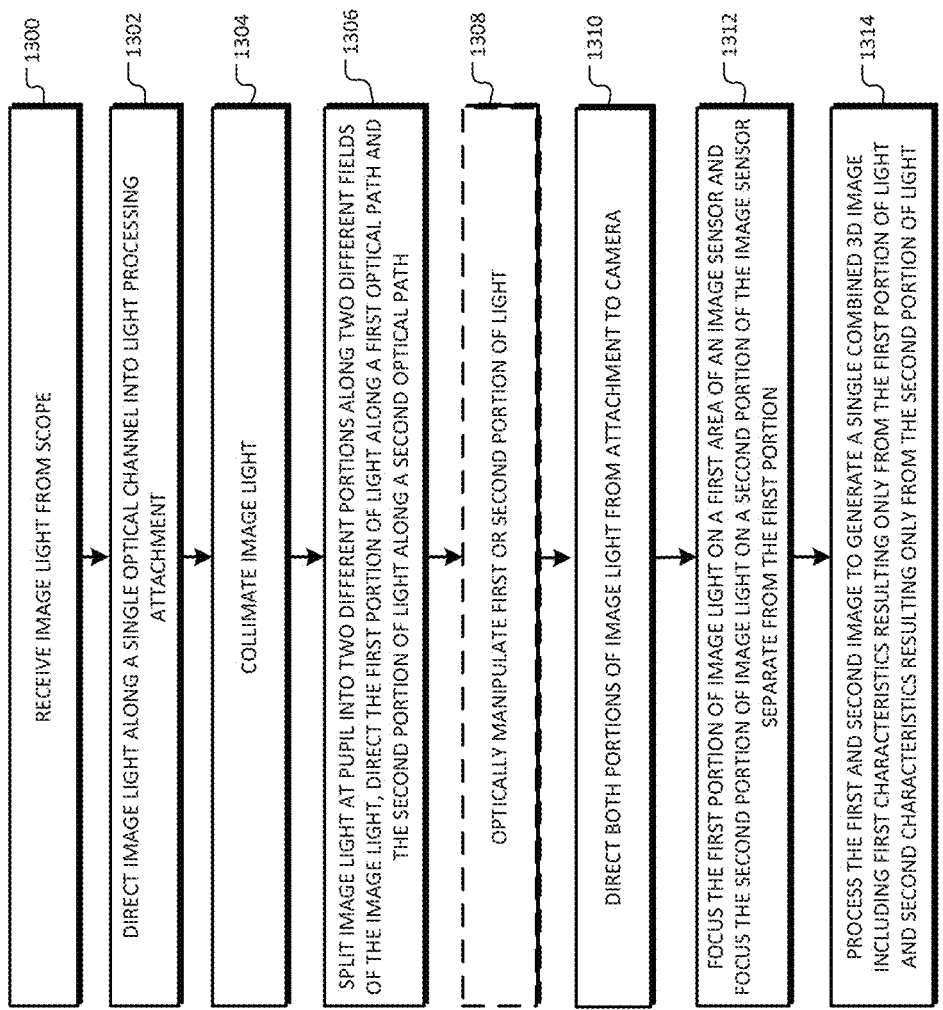
FIG. 13 is a flowchart of a process of operating the embodiment of FIG. 11 following its configuration.

FIG. 11 is a block diagram of a medical imaging system 10 according to another example embodiment of the invention providing an attachment with a pupil-splitting function allowing 3D imaging to be performed. FIG. 12 is a partial cross section diagram of optical assemblies 114 and 108 from attachment 101 and camera head 100 according to the embodiment of FIG. 11. FIG. 13 is a flowchart of a process of operating this embodiment following its configuration. The construction of endoscope 102 is similar to the other embodiments. Further, while an alternative camera head optical group 114 is shown in this version, a camera head 100 design as used in the other embodiments herein may also be employed with a pupil-splitting version of attachment 101, allowing multiple attachments to be interchanged on a single camera head 100. Referring to FIGS. 11-13, the optical assembly 108 starts with a collimating and directing lens group 113 of a single channel where the image light enters attachment 101 from endoscope 102 (block 1300), and is directed along a single optical channel to collimating and directing lens group 113 (block 1302). Next at block 1304, the process collimates the image light, in this version using lens groups 113 and 1102. Lens group 113 generally has negative power, while doublet lens 1102, including a convex-concave lens and a convex-convex lens, has positive power to complete the collimation, provide size and focus correction to the image light, and direct the image light to pupil splitter 1104. At block 1306, the process splits the image light at a pupil, using pupil splitter 1104 which is optically arranged to receive the image light in a collimated and substantially afocal state. Pupil splitter 1104 directs one half of the endoscope exit pupil light along one optical path and the other half along a different optical path and outputs them such that they are imaged by the camera head 100 onto two separate regions of image sensor 216. Pupil splitter 1104 in this version is constructed with two triangular prisms or a diamond-shaped prism designed to deviate the light from a first half of the pupil in one direction and the light from the other half of the pupil in a second direction. As is known in the art, the two halves of a pupil can be imaged separately to generate the two requisite images required for stereo imaging. The two optical paths along which the halves of the pupil are directed terminate as two separate images on the sensor. The collected stereo images, using conventional processing/formatting procedures, may then be used for 3D display. Following splitting the image light at pupil splitter 1104, the process may further optically manipulate one or both of the portions of light inside attachment 101, as shown at block 1308. Next at block 1310, the process directs both portions of light from attachment 101 to camera head 100.

Optically arranged to receive the both portions of light at camera head optical group 114 is a plano-convex lens 1105 having a slight positive power, which directs both portions of light to doublet lens 1106. Doublet lens 1106 has a slight negative power for aligning the two optical channels. Optically arranged to receive both portions of light from lens 1106 is a doublet lens including a bi-convex lens and a concave-convex lens and having a positive power, which serves to focus both portions of light appropriately toward image sensor 216. Optically arranged to receive both portions of light from lens 1108 is an optional flat plate 1110. Finally, both portions of light are directed to separate portions of image sensor 216, as shown at block 1312. In operation, the image processor receives data from the image sensor comprising two images from the respective portions of light, a 'left' image and a "right" image, and formats them for display as a single 3D image on a 3D monitor, as shown at block 1314.

Figure 14:
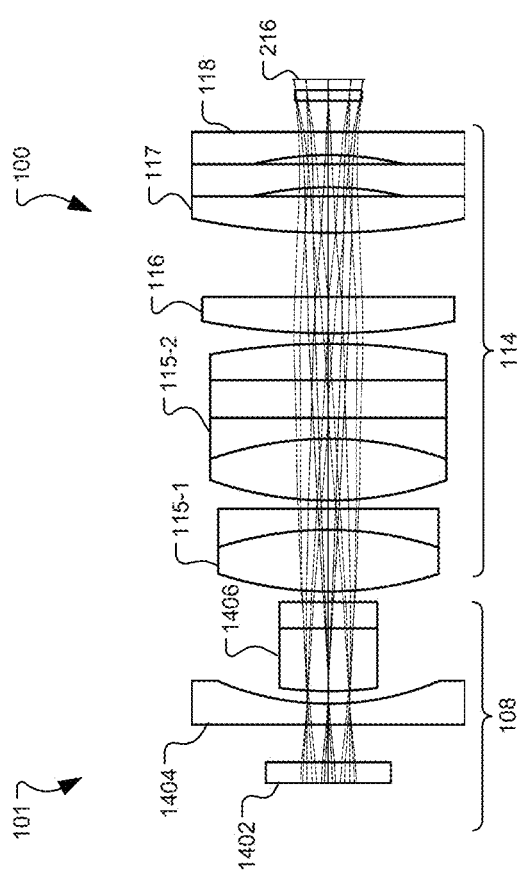
FIG. 14 is a partial cross section diagram of optical assemblies according to another embodiment in which a light processing attachment allows conventional endoscopy.

FIG. 14 is a partial cross section diagram of optical assemblies 114 and 108 from attachment 101 and camera head 100 according to another embodiment in which attachment 101 has optical elements that allow the attachment to be used with an endoscope to provide a conventional, single image to camera head 100. Attachment optical assembly 108 includes a cover glass 1402 at its distal end optically arranged to receive image light from an endoscope. Focusing lens 1404 is a plano-concave lens optically positioned to receive the incoming light and pass it to collimating lens 1406. Camera head optical group 114 is constructed similarly to the embodiments of FIG. 3 and FIG. 6. As can be understood, the lenses of camera head optical group 114 are preferably constructed larger than would be necessary for camera head 100 to operate directly attached to an endoscope, allowing for two light paths 301, 302 to be passed into camera head 100. As such, when using the same camera head 100 with an attachment 101 for conventional single-image endoscopy, it is advantageous to resize the image with focusing optics to allow the single image to use more area of image sensor 216. This allows a single camera head design to be employed with any of the attachment 101 designs provided herein, and other variations for attachment 101.

Figure 15:
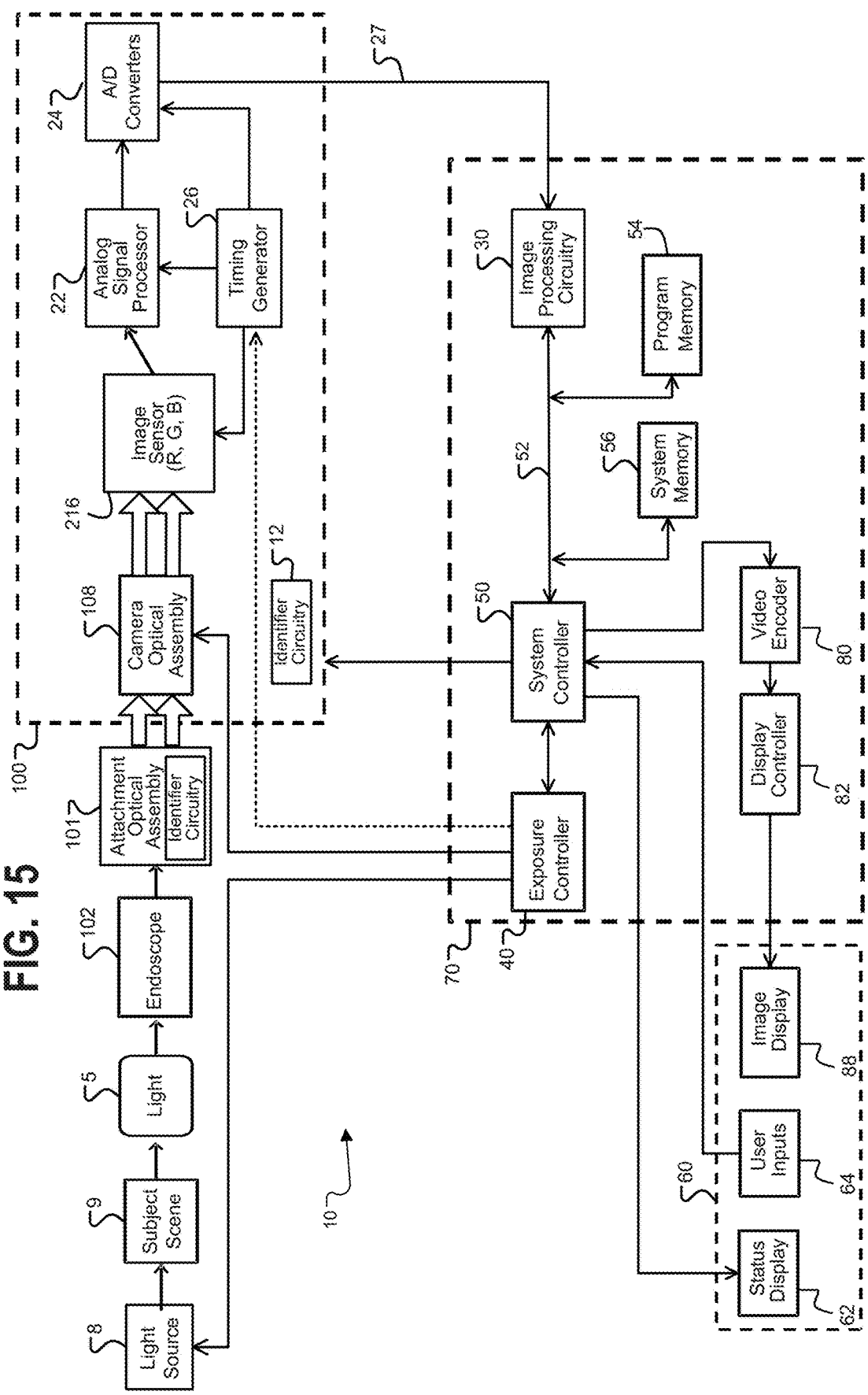
FIG. 15 is a hardware block diagram of system including an example image capture device according to an example embodiment of the invention.

Referring to FIG. 15, a block diagram of system including an endoscope 102, attachment 101, and an image capture device having an improved dual image optical path as described above. The depicted camera head 100 may be employed with multiple different attachments 101 provided according to the embodiments herein, and with additional attachments. As such, the depicted system 10 may, in different configurations, act as multiple different devices for image capture, such as an FI-capable endoscope, a 3D endoscope, or an enhanced depth-of-field endoscope, for example.

As shown in the diagram, a light source 8 illuminates subject scene 9 with visible light. Light source 8 may be part of attachment 101, endoscope 102, camera head 100, or may be provided by a separate, independent source. Fluorescent excitation light may also be used, which may be outside the visible spectrum in the ultra-violet range or the infra-red/near infrared range, or both. Light source 8 may include a single light emitting element configured to provide light throughout the desired spectrum, or a visible light emitting element and a one or more fluorescent excitation light emitting elements. Further, light source 8 may include fiber optics passing through the body of the scope, or other light emitting arrangements such as LEDs or laser diodes positioned at or near the front of the scope.

Attachment 101 includes an identifier circuit adapted to communicate identifying information for attachment 101 to camera head 100, or to camera control unit 70. As shown, camera head 100 includes identifier circuitry 12 adapted to receive the identifying information. Such identifying information is employed for reconfiguring the system to work with whichever supported attachment 101 is attached to camera head 100, for example according to the process of FIG. 16. Identifier circuitry 12 may be RFID reader circuitry for coupling with RFID tag identifier circuitry on attachment 101, or other suitable circuitry for communicating identifying information such as a serial number, or an identification of the type of attachment 101 being used. Any of the embodiments of attachment 101 herein will typically include identifier circuitry. The identification information is preferably passed to camera control unit 70 for use in configuring the system. For embodiments in which a light source is provided on attachment 101, wired or wireless power transfer circuitry may also be included on camera head 100 and attachment 101 to provide power to attachment 101.

In use, light 5 reflected from (or, alternatively, as in the case of fluorescence, excitation light absorbed and subsequently emitted by) the subject scene is received by endoscope 102 and directed to attachment 101. While in this version the light is split as described herein and focused to form two images at a solid-state image sensor 216, attachments 101 may be provided that do not split the light into two portions, and instead direct the image light along a single path from attachment 101 to camera head 100. According to the techniques and processes herein, such attachments 101 may be employed interchangeably with alternative attachments that split the light, providing ability to reconfigure camera head 100 to work with a variety of attachments 101 and endoscopes 102. Image sensor 216 converts the incident light to an electrical signal by integrating charge for each picture element (pixel). The image sensor 216 may be constructed with any suitable sensor technology such as active pixel complementary metal oxide semiconductor sensor (CMOS APS) or a charge-coupled device (CCD), for example.

The total amount of light 5 reaching the image sensor 216 is regulated by the light source 8 intensity, the light conditioning attachment's aperture size, the camera optical assembly 114 aperture size, and the time for which the image sensor 216 integrates charge. An exposure controller 40 responds to the amount of light available in the scene given the intensity and spatial distribution of digitized signals corresponding to the intensity and spatial distribution of the light focused on image sensor 216. If fluorescence imaging is used, exposure controller 40 also controls the emission of fluorescent excitation light from light source 8, and may control the visible and fluorescent light emitting elements to be on at the same time, or to alternate to allow fluoresced light frames to be captured in the absence of visible light if such is required by the fluorescent imaging scheme employed. Exposure controller 40 may also control the optical assembly 108 aperture, and indirectly, the time for which the image sensor 216 integrate charge. The control connection from exposure controller 40 to timing generator 26 is shown as a dotted line because the control is typically indirect.

Timing generator 26 produces various clocking signals to select rows and pixels and synchronizes the operation of image sensor 216, analog signal processor 22, and A/D converter 24. Camera head 100 includes the image sensor 216, the analog signal processor 22, the A/D converter 24, and the timing generator 26. The functional elements of the camera head 100 can be fabricated as a single integrated circuit as is commonly done with CMOS image sensors or they can be separately-fabricated integrated circuits.

Analog signals from the image sensor 216 are processed by analog signal processor 22 and applied to analog-to-digital (A/D) converter 24 for digitizing the analog sensor signals. The digitized signals each representing streams of images or image representations based on the data, are fed to image processor 30 as image signal 27. Typically, both images will be transmitted together in signal 27 as a single image, which is separated in the image processing circuitry into dual image areas of the sensor (for example, image 1 and image 2, of FIG. 17A and FIG. 17B).

The system camera control unit (CCU) 70 includes image processing circuitry 30 performing digital image processing functions to process and filter the received images as is known in the art. Image processing circuitry may include separate, parallel pipelines for processing the first and second images separately. CCU 70 may be implemented in a single assembly or may include two or more camera control modules performing different functions such as communication with a specific camera model, and image processing. Such circuitry is known in the art and will not be further described here. Image processing circuitry 30 may provide algorithms, known in the art, for combining two images of the same view but containing different characteristics in a combined image display.

The system controller 50 controls the overall operation of the image capture device based on a software program stored in program memory 54. This memory can also be used to store user setting selections and other data to be preserved when the camera is turned off. System controller 50 controls the sequence of data capture by directing exposure controller 40 to set the light source 8 intensity, the optical assembly 108 aperture, and controlling various filters in optical assembly 108 and timing that may be necessary to obtain image streams. A data bus 52 includes a pathway for address, data, and control signals.

Processed image data are continuously sent to video encoder 80 to produce a video signal. This signal is processed by display controller 82 and presented on image display 88. This display is typically a liquid crystal display backlit with light-emitting diodes (LED LCD), although other types of displays are used as well. The processed image data can also be stored in system memory 56 or other internal or external memory device.

The user interface 60, including all or any combination of image display 88, user inputs 64, and status display 62, is controlled by a combination of software programs executed on system controller 50. User inputs typically include some combination of typing keyboards, computer pointing devices, buttons, rocker switches, joysticks, rotary dials, or touch screens. The system controller 50 manages the graphical user interface (GUI) presented on one or more of the displays (e.g. on image display 88). In particular, the system controller 50 will typically have a mode toggle user input (typically through a button on the endoscope or camera head itself, but possibly through a GUI interface), and in response transmit commands to adjust image processing circuitry 30 based on predetermined setting stored in system memory. Preferably a system employed with any of the device designs herein provides ability to toggle between an individual view of either single image (for example, image 1 or image 2), both individual images, and/or a view of the combined image created with processing of data from both images. Settings may be provided to adjust the manner in which characteristics from the individual images are combined and displayed or stored. Settings may also include different settings for different models of scopes that may be attached to a camera head or other imaging device containing camera head 100.

Image processing circuitry 30 is one of three programmable logic devices, processors, or controllers in this embodiment, in addition to a system controller 50 and the exposure controller 40. Image processing circuitry 30, controller 50, exposure controller 40, system and program memories 56 and 54, video encoder 80, and display controller 82 may be housed within CCU 70.

CCU 70 may be responsible for powering and controlling light source 8, camera head 100, and/or optical assembly 108. In some versions, a separate front-end camera module may perform some of the image processing functions of image processing circuitry 30.

Although this distribution of imaging device functional control among multiple programmable logic devices, processors, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, or other digital logic circuit can be designated to perform all of the needed functions. All of these variations can perform the same function and fall within the scope of this invention.

Figure 16:
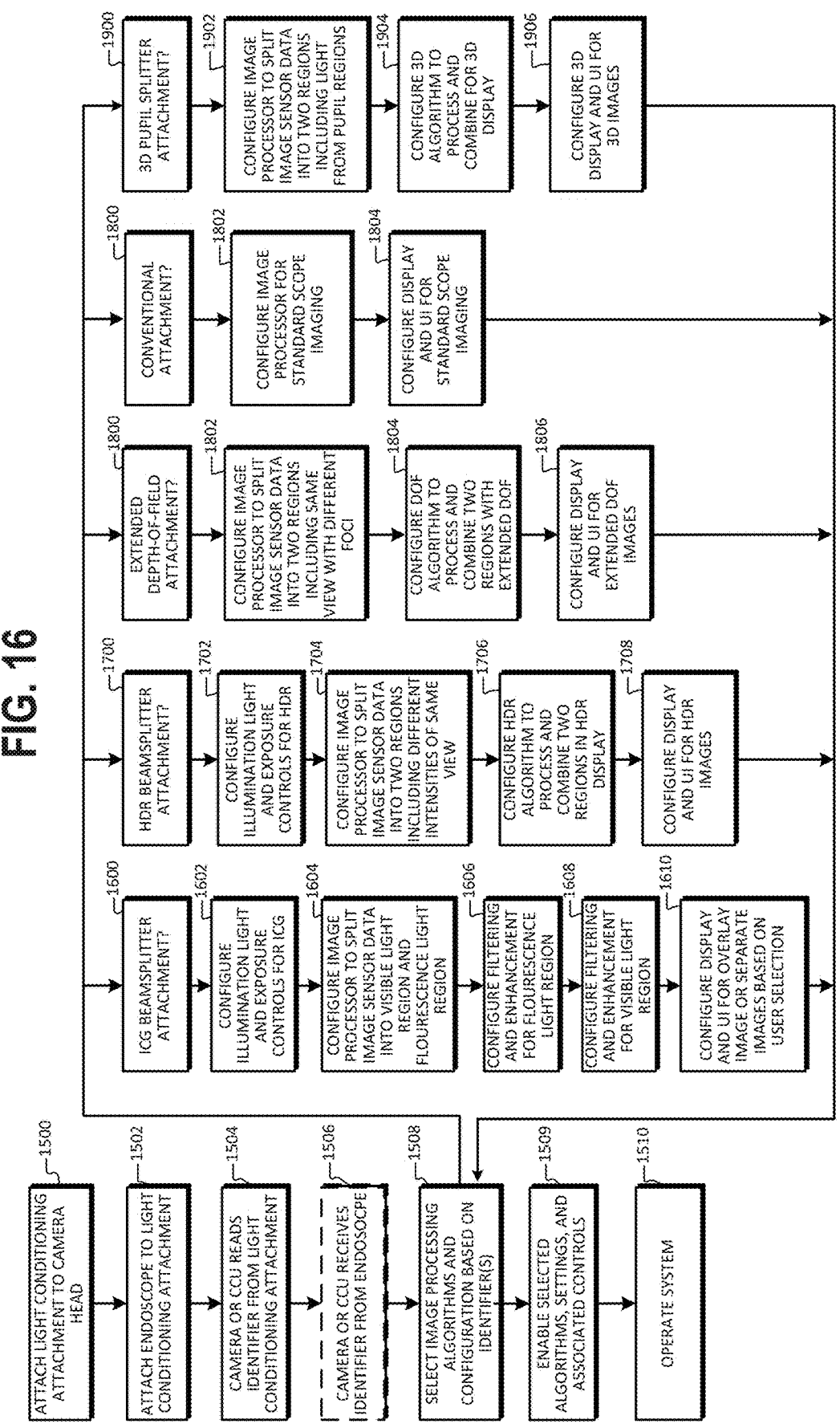
FIG. 16 is a flowchart showing an example process for recognizing attachments and reconfiguring the system according to an example embodiment of the invention.

FIG. 16 is a flowchart showing an example process for recognizing attachments 101 and reconfiguring the system accordingly. The depicted process may be used to operate a system such as the embodiment of FIG. 15, or other systems including multiple interchangeable attachments 101. The particular order is not limiting, and various embodiments may conduct the depicted steps in another order. The process begins at block 1500, where a selected light conditioning attachment 101 is attached to camera head 100. While a process is described herein, it should be understood the invention may be provided as a system including camera head and a set of light conditioning attachments 101, including all or some of the attachments 101 described herein. A suitable endoscope may also be provided as part of the system. At block 1502, an endoscope 102 is attached to the light conditioning attachment. At block 1504, the process includes the camera head or CCU receiving an identifier for the attached light conditioning attachment 101, preferably using the identifier circuitry of FIG. 15. The camera head, alone or in cooperation with an attached CCU, recognizes that a new light conditioning attachment has been attached to the camera head, or the user identifies the attachment through the CCM user interface. The recognition may happen with any suitable means such as an RFID tag being recognized, a serial number, or an optical identifier such as a bar code, or two dimensional barcode (or QR code), or other identifier being read from the light conditioning attachment. At block 1506, an identifier for the attached endoscope may also be received. Next at block 1508, responsive to the received attachment identifier, the process selects image processing algorithms and system configuration settings to be used in operation. Various options for these are depicted for different cases of the identifier received.

Based on receiving an identifier for an ICG beamsplitter attachment, the process at block 1600 moves to block 1602 where it configures the illumination light source 8 and the camera head exposure controls for ICG imaging. Next at block 1604, the process configures the CCU image processor to split the image sensor data into a visible light region and a fluorescence light region. Next the imaging processing algorithms are configured for filtering and enhancement of the two different light regions at blocks 1606 and 1608. This may include configuring two separate image processing pipes within the CCU image processing circuitry 30. At block 1610, the process configures the system display and user interface software to display. This may be based on user selections, such as by presenting to the user, via the UI, an indication of which attachment is attached, and presenting to the user any manual controls specific to this attachment. In one version, per user selection, the CCU 70 will calculate a (1) conventional white light image (2) a grey scale or pseudocolor fluorescence image (3) a conventional or grey scale white light image with pseudocolor fluorescence overlay, or (4) a white light image and a separate fluorescence image to be displayed on two separate monitors. The process then enables and activates the settings and controls at block 1509 and the system is operated in the new configuration at block 1510.

Referring again to block 1508, in the case that an HDR beamsplitter attachment identifier is received, the process at block 1700 goes to block 1702 where it configures the illumination light source 8 and camera head 100 exposure controls for HDR imaging. At block 1704, the process configures the image processing circuitry of CCU 70 to split the image data into two regions for HDR processing. Next at block 1706, the process configures the HDR algorithm to process and combine the two regions according to known HDR techniques in which variations at low intensities and high intensities are enhanced and mapped onto a higher dynamic range image. At block 1708, the process configures the display and user interface for HDR images, and returns to block 1509 where the settings are all enabled. Next, the system is ready for operation at block 1510.

Back at block 1508, if an extended depth-of-field attachment identifier is received, the process at block 1800 goes to block 1802 where it configures the CCU image processing circuitry to split the image sensor data into two regions, including the same view area but with different focal conditions. Next at block 1804, the process configures a known depth-of-field combining algorithm for combining images from the two regions, typically by combining the data to provide the most in-focus view available from either of the images for a particular area of the observed scene so as to produce an image with extended depth of field compared to a conventional imaging system. At block 1806 the process configures the system display and user interface for display of extended depth-of-field images. These settings are enabled at block 1509, and the system is operated with the new configuration at block 1510.

If a conventional (single image) attachment identifier is received, the process at block 1800 goes to block 1802 where it configures the CCU image processor for conventional endoscope imaging. At block 1803, the system display and user interface are likewise configured for conventional imaging, and the process at block 1509 enables these settings allowing operation of the system with the new configuration at block 1510.

If at block 1508 a 3D pupil splitter attachment identifier is received, the process at block 1900 goes to block 1902. Here it configures the CCU image processing circuitry to separate the image sensor data into two regions, for creating from the split the images two images, a 'left' image and a "right" image. Next at block 1904, the process configures known 3D imaging algorithms for processing the left and right images and formatting them for display as a single 3D image on a 3D monitor. At block 1906, the process configures a 3D system display and user interface for displaying performing operations on the 3D images. These settings are then enabled at block 1509, allowing the system to operate with the new configuration at block 1510.

Figure 17A:
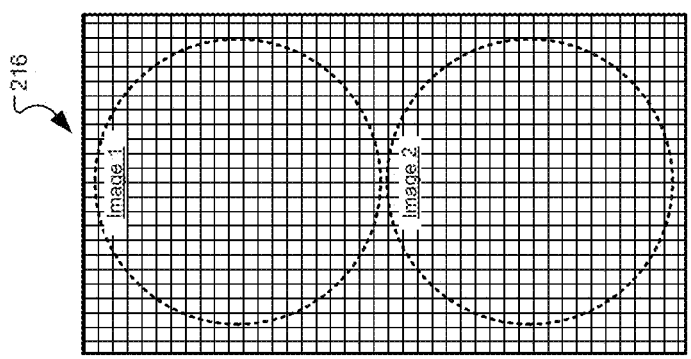
FIGS. 17A-17B are diagrams showing examples of sensor area usage with various image projection designs.
Figure 17B:
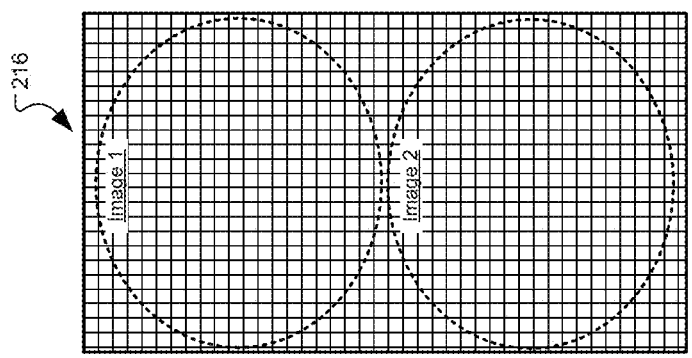

FIGS. 17A and 17B show two different image detection arrangements at rectangular image sensor 216. Dual image systems according to the present invention, as shown in FIG. 17A, utilize a large number of available pixels and enable all of the benefits discussed above associated with capturing two versions of the same scene. FIG. 17B shows a still more improved result by combining both the benefits of the anamorphic aspect ratio as well as the capturing of two images simultaneously, making, thereby maximal use of a single image sensor. It is noted that such anamorphic ratio may be used with any of the embodiments herein.

As used herein the terms "comprising," "including," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

The invention claimed is:

1. A system for modifying light passing from a medical scope to a camera, the system comprising:
 a camera having a distal end and an image sensor;
 a first light conditioning attachment including:
  a body including an optical portal, the body having a proximal end adapted to be attached to and detached from the camera's distal end, and a distal end adapted to be attached to and detached from the medical scope, the optical portal positioned to allow light from the medical scope to pass from the medical scope to the image sensor of the camera;
  an optical assembly optically positioned between the proximal and distal ends, including a collimation lens group and an optical group including a beam splitter or a pupil splitter, the collimation lens group operable to receive image light from the medical scope in a substantially afocal state and increase collimation of the image light through refraction, the optical group operable to receive the image light from the collimation lens group and with the image light substantially afocal, split the image light into a first portion of image light and a second portion of image light, and direct the first portion of image light along a first optical path and the second portion of image light along a second optical path; and
  an identification indicator adapted to be recognized by the camera or a camera control unit;
 wherein the camera further comprises a lens aperture sized to receive light from the first and second optical paths, and a lens group operable to focus the first portion of image light on a first area of the image sensor and focus the second portion of image light on a second portion of the image sensor separate from the first portion; and
 wherein the camera control unit is adapted to recognize, by means of the identification indicator, when the first light conditioning attachment is attached to the camera's distal end and when a second light conditioning attachment is attached to the camera's distal end, and in response to recognizing the first light conditioning attachment, selecting and enabling image processing algorithms specific to the first light conditioning attachment for processing image data from the image sensor.

2. The system of claim 1, further comprising the second light conditioning attachment, wherein the second light conditioning attachment has a different light conditioning function, and a different associated identification indicator, than the first light conditioning attachment.

3. The system of claim 1, in which the beam splitter of the first light conditioning attachment is operable to split the image light with spectral selectivity, whereby the spectral content of the first portion of image light differs substantially from the spectral content of the second portion of image light.

4. The system of claim 3, wherein the first portion of image light comprises infrared content and the second portion of image light comprises visible light.

5. The system of claim 1, in which the first light conditioning attachment comprises a pupil splitter adapted to split the image light with the pupil splitter into the first portion of image light and the second portion of image light, thereby enabling the camera to provide 3D imaging.

6. The system of claim 1, wherein the first light conditioning attachment's optical assembly further comprises, along the first optical path, a lens selected to alter a focal plane of an image produced by the first portion of image light relative to a focal plane of an image produced by the second portion of image light, thereby enabling the camera to provide extended depth of field imaging.

7. The system of claim 1, wherein the camera's lens group comprises a Petzval lens and a field flattener.

8. The system of claim 1 further comprising, along the first optical path, a magnifying element such that the first and second portions of image light have different magnifications.

9. The system of claim 1, wherein the first light conditioning attachment is configured such that the first and second portions of image light have different intensities, enabling thereby high dynamic range imaging.

10. A method of producing endoscopy images, comprising the steps of:
 recognizing, on an electronic processor associated with a camera head, that a first light conditioning attachment has been attached to the camera head;
 in response to recognizing the first light conditioning attachment has been attached, selecting and enabling image processing algorithms in a camera control module, the image processing algorithms specific to the first light conditioning attachment and configured for processing an image data from an image sensor on the camera head;
 directing image light from a medical scope along a single optical channel to the first light conditioning attachment;
 in the first light conditioning attachment, receiving the image light from the medical scope in a substantially afocal state, and increasing collimation of the image light through refraction;
 in the first light conditioning attachment, splitting the image light from the single optical channel into a first portion of image light and a second portion of image light, and directing the first portion of light along a first optical path and the second portion of image light along a second optical path; and
 in the camera head, receiving the image light through a lens aperture sized to receive light from the first and second optical paths, and focusing the first portion of image light on a first area of the image sensor and focusing the second portion of image light on a second portion of the image sensor separate from the first portion generating, thereby, the image data from the image sensor; and
 transmitting the image data from the image sensor to the camera control module and, on the camera control module, processing the image data from the image sensor according to the enabled image processing algorithms.

11. The method of claim 10, in which the step of recognizing that the first light conditioning attachment has been attached to the camera head further comprises reading an RFID identifier from the first light conditioning attachment.

12. The method of claim 10, in which the step of recognizing that the first light conditioning attachment has been attached to the camera head further comprises reading an optical identifier tag for the first light conditioning attachment.

13. The method of claim 10, in which the step of recognizing that the first light conditioning attachment has been attached to the camera head further comprises receiving an electronic identification signal from the first light conditioning attachment.

14. The method of claim 10, further comprising:
recognizing, on the electronic processor, that a second light conditioning attachment has been attached to the camera head; and
in response to recognizing the second light conditioning attachment has been attached, selecting and enabling second image processing algorithms in the camera control module, the second image processing algorithms specific to the second light conditioning attachment and configured for processing the image data from the image sensor.

15. The method of claim 10, further comprising spectral filtering the image light whereby the spectral content of the first portion of light differs substantially from the spectral content of the second portion of light.

16. The method of claim 15, wherein the first portion of light comprises infrared content and the second portion of light comprises visible light.

* * * * *